US006306602B1

(12) United States Patent
Sillekens et al.

(10) Patent No.: US 6,306,602 B1
(45) Date of Patent: *Oct. 23, 2001

(54) OLIGONUCLEOTIDES THAT CAN BE USED IN THE AMPLIFICATION AND DETECTION OF CMV NUCLEIC ACID

(75) Inventors: Peter Theodorus Gerardus Sillekens, Gemonde; Eveline Catharina Anna Clasina Timmermans, Diessen, both of (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/465,945

(22) Filed: Dec. 17, 1999

Related U.S. Application Data

(63) Continuation of application No. 08/897,077, filed on Jul. 18, 1997, now Pat. No. 6,010,847, which is a continuation-in-part of application No. 08/628,654, filed on Mar. 27, 1996, now abandoned.

(51) Int. Cl.$^7$ ...................................................... C12Q 1/68
(52) U.S. Cl. ............................ 435/6; 435/91.2; 536/22.1; 536/24.3
(58) Field of Search ...................... 435/91.2, 6; 536/22.1, 536/24.3

(56) References Cited

U.S. PATENT DOCUMENTS 6,010,847 * 1/2000 Sillikens et al. .......................... 435/5

FOREIGN PATENT DOCUMENTS

| 0329822 | 8/1989 | (EP) . |
| 0586011 | 3/1994 | (EP) . |
| WOA 9313227 | 7/1993 | (WO) . |

OTHER PUBLICATIONS

Davis et al. Nucleotide sequence of a human cytomegalovirus DNA fragment encoding a 67–kilogalton phosphorylated viral protein, J. Virology. vol. 56(1), pp. 7–11, 1985.*

Pande et al. Genomic localization of the gene encoding a 32–kDa capsid protein of human cytomegalovirus, Virology, vol. 167, pp. 306–310, 1988.*

J. Gozlan et al., *Journal of Clinical Microbiology*, 31:7:1943–1945, 1993.

A. Bitsch et al., *The Journal of Infectious Diseases*, 167:740–743, 1993.

G. Gerna et al., *Journal of Clinical Microbiology*, 30:5:1232–1237, 1992.

Meyer et al., *Mol Cell Probes*, 8(4):261–271, Aug. 1994.

Schrier et al., *Science*, 230:1048–1051, 1985.

Davis et al., *J. Virol.*, 56(1):7–11, 1985.

Pande et al., *Virology*, 117:306–310, 1988.

Gozlan et al., *J. Virol. Methods*, 40:1–10, 1992.

DeGraaf et al., "Biochemical diversity in a phage display library of random decapeptides" *Gene* 128:13–17, 1993.

Chou, S., "Effect of Interstrain Variation in Diagnostic DNA Amplification of the Cytomegalovirus Major Immediate–Early Gene Region" *Journal of Clinical Microbiology*, 30(9): 2307–2310, Sep. 1992.

Beck et al., "An HCMV reading frame which has similarity with both the V and C regions of the TCRy chain", *DNA Sequence*, 2: 33–38, 1991.

* cited by examiner

*Primary Examiner*—W. Gary Jones
*Assistant Examiner*—Joyce Tung
(74) *Attorney, Agent, or Firm*—Myers Bigel Sibley & Sajovec

(57) ABSTRACT

The sensitivity and reliability (robustness) of CMV mRNA detection is greatly dependent on the selection of suitable oligonucleotides for amplification, since there is sequence variation among strains of CMV potentially in every region of the genome. The present invention is concerned with oligonucleotides that can be used in the amplification and detection of human Cytomegalovirus (HCMV) mRNA. These novel oligonucleotides show an improved sensitivity and robustness of CMV mRNA detection if compared with known sequences when used in amplification and detection. Furthermore a method for the diagnosis of HCMV disease is provided.

4 Claims, No Drawings

OLIGONUCLEOTIDES THAT CAN BE USED IN THE AMPLIFICATION AND DETECTION OF CMV NUCLEIC ACID

This application is a continuation of U.S. application Ser. No. 08/897,077, filed Jul. 18, 1997 (issued as U.S. Pat. No. 6,010,847), which is a continuation-in-part of U.S. application Ser. No. 08/628,654, filed Mar. 27, 1996 (abandoned), which claims the benefit under 35 U.S.C. § 371 from PCT Application No. PCT/EP95/03295, filed Aug. 18, 1995, which claims the benefit of European Application 94202360.7, filed Aug. 18, 1994.

FIELD OF THE INVENTION

The present invention is concerned with oligonucleotides that can be used in the amplification detection of human Cytomegalovirus (HCMV) mRNA. Furthermore a method for the diagnosis of HCMV disease is provided.

BACKGROUND OF THE INVENTION

Human Cytomegalovirus is an ubiquitous Herpes-type virus, having a double stranded DNA genome of about 240,000 nucleotides in length that infects 40–80% of humans before puberty. A prominent feature common to all herpesviruses is their establishment of lifelong persistence after infection and their ability to cause recurrent infection after reactivation (Stevens, J. G. Microbiol. Rev. 53, 318–332., 1989). HCMV also becomes latent after primary infection which often occurs without clinical symptoms. Even recurrent infection in most cases goes asymptomatic or leads to only mild disease in the immunocompetent host. However, in congenitally infected infants and immunocompromised patients, such as allograft recipients (Meyers, J. D., et al., J. Infect. Dis. 153, 478–488., 1986) or AIDS patients (Drew, W. L. J Infect. Dis 158, 449–456., 1988; Drew, W. L. Clin. Infect. Dis 14, 608–615., 1992), where the fine balance between the immune system and the latently existing virus is disturbed, HCMV may cause severe and sometimes life-threatening disease, including retinitis, gastrointestinal disorders, and encephalitis (Drew, 1992). Early administration of antiviral drugs like ganciclovir and foscarnet can have significant beneficial effects on the prognosis of a patient (Jahn, G. et al., Intervirology 35, 60–72., 1993; Schmidt, G. M. et al., N. Engl. J Med. 324, 1005–1011., 1991). Therefore, with the availability of clinically effective antiviral therapy, early and sensitive diagnosis is of significant importance.

CMV specific antibodies, in particular IgM antibodies, can be used as a marker for CMV infection, but are of limited value when it comes to discrimination between latent and active infections. Most viral detection methods currently employed do not unambiguously allow for prediction of whether a given infection will be symptomatic. Furthermore serological methods are indirect and often lack sensitivity. Viral culture is a more direct diagnostic parameter for CMV viremia. Although CMV culture from blood cells appeared to be indicative for an active CMV infection, the method does not enable rapid diagnosis and is technically difficult. Moreover, viral culture does not necessarily correspond to HCMV disease. A reliable relation between virus isolation from peripheral leukocytes and the appearance of clinical symptoms may not exist in some immunosuppressed patients (Delgado, R. et al., J Clin. Microbiol. 30, 1876–1878., 1992). Also urinary or pharyngeal shedding of the virus frequently occurs without clinical symptoms and organ involvement. Amplification of HCMV DNA in peripheral leukocytes by polymerase chain reaction (PCR), although a very sensitive technique for CMV viremia, is not usable as a marker of clinically symptomatic HCMV infection either. Due to the high sensitivity of enzymatic amplification, occasionally HCMV DNA was detectable in peripheral leukocytes without HCMV-related disease. Latent viral genomes may be detected by this technique or a patient may remain HCMV-DNA positive over a prolonged period of time after the disease has resolved (Jahn, G. et al., 1993; Zipeto, D. et al., J Clin. Microbiol. 30, 527–530., 1992; Delgado et al., 1992).

At the moment, the method of choice for the early diagnosis of acute symptomatic HCMV infection is the antigenemia assay based on immunological detection of the structural protein pp65 by using specific antibodies (Storch, G. A., et al., J. Clin. Microbiol. 32, 997–1003., 1994; Gerna, G. et al., J. Infect. Dis. 164, 488–498., 1991; Gerna, G., et al., J Clin. Microbiol. 30, 1232–1237.98., 1992). However, a matter of concern employing this method is its sensitivity. The number of pp65-positive cells in the early course of infection may be very low. Furthermore, in expressing cells stability of the pp65 antigen appeared to be limited (Chou, S., Curr. Opin. Infect. Dis. 5, 427–432., 1991) and sensitivity can be reduced due to the application of monoclonal antibodies rather than a pool of anti-pp65 antibodies that would recognize different epitopes of the protein.

Since viral replication requires transcription of mRNA species, the use of HCMV mRNA detection as a marker for active CMV infection was investigated (Bitsch, A. et al., J Infect. Dis 167, 740–743, 1993.

Recently, HCMV infections were examined on the transcript level using RNA amplification (Bitsch, A. et al., 1993; Meyer, T. et al., Mol. Cell Probes. 8, 261–271., 1994; Gerna, G., et al., J Clin. Microbiol. 30, 1232–1237.98, 1993; Gerna, G., et al., J Clin. Microbiol. 30, 1232–1237.98, 1992). In principle, like detection of viral antigens, analysis of viral transcripts expressed in association with viral replication should allow reliable diagnosis of symptomatic infections.

More recently, the detection of certain mRNA's of HCMV i.e. based on IEA (immediate early antigen) and the matrix tegument protein pp67 mRNA have been described in U.S. Ser. No. 08/628,654. However, the novel oligonucleotides of the present invention have several advantages over the oligonucleotides as disclosed in the previous application. Comparison studies are presented in the experimental part of the description.

The sensitivity and reliability (robustness) of CMV mRNA detection is greatly dependent on the selection of the oligonucleotides used in the amplification, since there is sequence variation among strains of CMV potentially in every region of the genome. Ideally, primer selection should be based on knowledge of interstrain variability in candidate primer sequences and the consequences of mismatching at primer sites. (Chou S., J. of Clin. Microbiol., 2307–2310, 1992).

Therefore, the need exists for suitable oligonucleotides including nucleic acid sequences that can be used as in the amplification and subsequent detection of all strain variants of CMV.

SUMMARY OF THE INVENTION

The present invention is related to the detection of a certain late HCMV mRNA and provides oligonucleotides suitable for use in the amplification and subsequent detection of this mRNA. The binding sites of the oligonucleotides according to the present invention are located in the matrix tegument protein pp67 encoding gene sequence (UL65), which is expressed during the late phase of CMV infection.

Preferred oligonucleotides according to the present invention, correspond to part of a nucleic acid sequence encoding HCMV pp67, said oligonucleotide being 10–35 nucleotides in length and comprising at least a fragment of 10 nucleotides of a sequence selected from the group consisting of:

5'-GGGTCGATTCAGACTGA-3' [SEQ.ID.No.: 10];

5'-CTGGAGATATATGTTGACCA-3' [SEQ.ID.No.: 11],

5'-GGATTCGGACTTTCCGTTCGA-3' [SEQ.ID.No.: 8], and

5'-CCAAAAAGCTAGCCGTCACG-3' [SEQ.ID.No.: 12], or its complementary sequence.

A preferred embodiment of the present invention is directed to an oligonucleotide linked to a promoter sequence.

DETAILED DESCRIPTION OF THE INVENTION

An example of oligonucleotide pairs according to the present invention includes the following oligonucleotide sequences:

5'-aattctaatacgactcactatagggagaGGGTCGATTCAGACTGA-3' [SEQ ID NO: 9] or

5'-aattctaatacgactcactatagggagaGGGTCGATTCGAGACCGA-3' [SEQ ID NO: 5] in combination with 5'-GACCTGATATCCCTCCATATA-3' [SEQ ID NO: 7]. (The T7 promoter sequence is shown, but may be replaced by any other suitable promoter sequence.) A probe that may be used for the detection of the amplificate generated using this pair may comprise an oligonucleotide consisting essentially of the following sequence: 5'-GGATTCGGACTTTCCGTTCGA-3' [SEQ ID NO: 8]. Probes comprising said sequence are also part of the present invention.

For the pp67 gene sequence interstrain variations between CMV AD169 and Towne exist. Therefore, for this target two oligonucleotide pairs were chosen, CMV-pp67-1 and CMV-pp67-4 (Table 1) either of which was derived from the same region of the gene but each based on a different laboratory strain. An example of oligonucleotides for the detection of pp67 mRNA are oligonucleotides, 10–35 nucleotides in length comprising, at least a fragment of 10 nucleotides, of a sequence selected from the group consisting of:

5'-GGGTCGATTCAGACTGA-3' [SEQ ID NO:10]

5'-GGGTCGATTCGAGACCGA-3' [SEQ ID NO: 6]; and

5'-GACCTGATATCCCTCCATATA-3' [SEQ ID NO: 7].

A preferred embodiment of the present invention is directed to the following oligonucleotide sequences:
5'-aattctaatacgactcactatagggagaGGGTCGATTCAGACTGA-3' [SEQ ID NO: 9] in combination with 5'-CTGGAGATATATGTTGACCA-3' [SEQ ID NO:11], for the amplification. (The T7 promoter sequence is shown, but may be replaced by any other suitable promoter sequence.) In this preferred embodiment of the present invention, an oligonucleotide consisting essentially of the sequence 5'-GGATTCGGACTTTCCGTTCGA-3' [SEQ ID NO: 8] or 5'-CCAAAAAGCTAGCCGTCACG-3' [SEQ ID NO:12], provided with a detectable label, is the the preferred probe for the detection of the amplificate generated using the preferred oligonucleotides according to the present invention.

An oligonucleotide sequence used as a detection probe may be labeled with a detectable moiety. Various labeling moieties are known in the art. Said moiety may, for example, either be a radioactive compound, a detectable enzyme (e.g. horse radish peroxidase (HRP)) or any other moiety capable of generating a detectable signal such as a calorimetric, fluorescent, chemiluminescent or electrochemiluminescent signal. Preferred analysis systems wherein said labels are used are electrochemiluminescence (ECL) based analysis or enzyme linked gel assay (ELGA) based analysis.

As already indicated above, and will be presented in the experimental part of the description, both the sensitivity and reliability of CMV mRNA detection is greatly improved using the oligonucleotides according to the present invention when compared to known oligonucleotides used in this art.

The term "loligonucleotide" as used herein refers to a molecule comprised of two or more deoxyribonucleotides or ribonucleotides such as primers and probes.

The term "primer" as used herein refers to an oligonucleotide either naturally occurring (e.g. as a restriction fragment) or produced synthetically, which is capable of acting as a point of initiation of synthesis of a primer extension product which is complementary to a nucleic acid strand (template or target sequence) when placed under suitable conditions (e.g. buffer, salt, temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least about 10 nucleotides in length of a sequence substantially complementary (P1) or homologous (P2) to the target sequence, but somewhat longer primers are preferred. Usually primers contain about 15–26 nucleotides but longer primers may also be employed.

Normally a set of primers will consist of at least two primers, one 'upstream' and one 'downstream' primer which together define the amplificate (the sequence that will be amplified using said primers).

The oligonucleotides according to the invention may also be linked to a promoter sequence. The term "promoter sequence" defines a region of a nucleic acid sequence that is specifically recognized by an RNA polymerase that binds to a recognized sequence and initiates the process of transcription by which an RNA transcript is produced. In principle any promoter sequence may be employed for which there is a known and available polymerase that is capable of recognizing the initiation sequence. Known and useful promoters are those that are recognized by certain bacteriophage RNA polymerases such as bacteriophage T3, T7 or SP6.

It is understood that oligonucleotides consisting of the sequences of the present invention may contain minor deletions, additions and/or substitutions of nucleic acid bases, to the extent that such alterations do not negatively affect the yield or product obtained to a significant degree.

Another preferred embodiment of the present invention is directed to a method for the diagnosis of symptomatic CMV disease, wherein the presence of pp67 mRNA encoding a late structural protein of the human Cytomegalovirus in a blood sample of an individual, suspected of carrying said disease, is detected, said method comprising the following steps:

amplifying a target sequence within said mRNA using oligonucleotides according to the invention and suitable amplification reagents, reacting the sample, optionally containing amplified nucleic acid, with an oligonucleotide according to the present invention as a detection probe, detecting hybrids formed between the amplified sequence and the probe.

Various techniques for amplifying nucleic acid are known in the art. One example of a technique for the amplification of a DNA target segment is the so-called "polymerase chain reaction" (PCR). With the PCR technique the copy number of a particular target segment is increased exponentially with a number of cycles. A pair of primers is used and in each cycle a DNA primer is annealed to the 3' side of each of the two strands of the double stranded DNA-target sequence. The primers are extended with a DNA polymerase in the presence of the various mononucleotides to generate double stranded DNA again. The strands of the double stranded DNA are separated from each other by thermal denaturation and each strand can serves as a template for primer annealing and subsequent elongation in a following cycle. The PCR method has been described in Saiki et al., Science 230, 135, 1985 and in European Patents no. EP 200362 and EP 201184.

Another technique for the amplification of nucleic acid is the transcription based amplification system (TAS). TAS employs an RNA-transcript-production step from a DNA, synthesized to incorporate a segment of the target sequence and a promoter, to enable transcription from the segment of a RNA with the sequence complementary to that of the target. Multiple cycles can be carried out as the RNA made in the transcription step can serve as template for making similarly transcribable DNA, which in turn, can be transcribed to yield additional RNA. The TAS method is described in International Patent Appl. no. WO 88/10315. Transcription based amplification techniques usually comprise treating target nucleic acid with two oligonucleotides one of which comprises a promoter sequence, to generate a template including a functional promoter. Multiple copies of RNA are transcribed form said template and can serve as a basis for further amplification.

An isothermal continuous transcription based amplification method is the NASBA (nucleic acid sequence based amplification) process, as described in European Patent no. EP 329822. NASBA includes the use of T7 RNA polymerase to transcribe multiple copies of RNA from a template including a T7 promoter.

For RNA amplification (as with the method according to the invention), the NASBA technology or other transcription based amplification techniques are preferred.

If RT-PCR is used for the detection of viral transcripts differentiation of mRNA- and DNA-derived PCR products is necessary. For spliced transcripts, like the IEA mRNA, the exon-intron structure can be used. However, mRNA species encoding the late structural proteins are almost exclusively encoded by unspliced transcripts. DNAse treatment prior to RT-PCR can be employed (Bitsch, A. et al., J Infect. Dis 167, 740–743., 1993; Meyer, T. et al., Mol. Cell Probes. 8, 261–271., 1994), but sometimes fails to remove contaminating DNA sufficiently (Bitsch, A. et al., 1993). In contrast to RT-PCR, NASBA, which is based on RNA transcription by T7 RNA polymerase (Kievits et al., 1991; Compton, 1991), does not need differentiation between RNA- and DNA-derived amplification products since it only uses RNA as its principal target. NASBA enables specific amplification of RNA targets even in a background of DNA. Especially for unspliced targets like almost all late HCMV gene transcripts, this method is beneficial as it circumvents DNAse treatment which occasionally might be inefficient (Bitsch, A. et al., 1993). This method was used for the analysis of CMV transcripts in whole blood samples from HIV-infected individuals.

Test kits for the detection of CMV in clinical samples are also part of the present invention. A test kit according to the invention may comprise a pair of oligonucleotides according to the invention and a probe comprising an oligonucleotide according to the invention. Such a test kit may additionally comprise suitable amplification reagents such as DNA and or RNA polymerases and mononucleotides. Test kits that can be used with the method according to the invention may comprise the oligonucleotides according to the invention for the amplification and subsequent detection of pp67 mRNA. A preferred embodiment for the test kit comprises the oligonucleotides:

5'-aattctaatacgactcactatagggagaGGGTCGATTCAGAC TGA-3' [SEQ ID NO: 9] in combination with 5'-CTGGAGATATATGTTGACCA-3' [SEQ ID NO:11] for the amplification, and 5'-GGATTCGGACTTTCCGTTCGA-3' [SEQ ID NO: 8] or 5'-CCAAAAAGCTAGCCGTCACG-3' [SEQ ID NO:12], provided with a detectable label, as probe.

The invention is further exemplified by the following examples.

EXAMPLES

Example 1

Analysis of CMV DNA and mRNA in Clinical Samples.

1.1 MATERIALS AND METHODS 1.1.1 Clinical Specimens

Samples from patients clinically at risk of infection with CMV were analyzed for the presence of mRNAs encoding the immediate early antigen (IEA) or the matrix tegument protein pp67 expressed during the late phase of CMV infection.

The thirty-five blood samples were obtained from immunocompromised patients including 22 heart, liver, or kidney transplant recipients, 8 AIDS patients, two patients with leukemia, one patient with a myelodysplastic syndrome, one patient with primary Epstein Barr virus mononucleosis, and one patient with Kaposi sarcoma. Ethylenediamine tetraacetic acid (EDTA) anticoagulated blood samples submitted consecutively as received by the laboratory, were mixed with nine volumes of lysis buffer [50 mM Tris-Hydrochloric acid (pH 6.4); 20 mM EDTA; 1.3% (w/v) Triton X-100; 5.25 M guanidinium thiocyanate] and stored at −70° C. until use.

1.1.2 Nucleic acid isolation

From the anticoagulant-treated blood specimens total nucleic acid was isolated using guanidinium thiocyanate-mediated cell lysis and adsorption of nucleic acid to silica particles (Boom et al., J. of Clin. Microbiol. 28, 495–503, 1990).

Whole blood samples in lysis buffer were thawed and from each sample 1 ml (equivalent to 100 µl whole blood) was transferred into an Eppendorf tube. Subsequently, 70 µl of hydrochloric acid-activated silicum dioxide particles [size-selected suspension of 1 mg/ml in 0.1 M Hydrochloric acid (Sigma); see ref. Boom et al., 1990] were added and the suspension was incubated during 10 minutes at room temperature with regular vortexing. Nucleic acid bound to the silica was spun down by centrifugation. Pelleted silica particles were washed twice with 1 ml GuSCN wash buffer [50 mM Tris-hydrochloric acid (pH 6.4); 5.25 M guanidinium thiocyanate], followed by two washing steps with 1 ml 70% ethanol and a single washing step with 1 ml acetone. After each washing step, the suspension was briefly centrifuged and the silica pellet was resuspended in the next washing solution by thorough mixing. After removal of the acetone, the silica particles were dried by incubation at 56° C. in a heating block during 10 minutes. Nucleic acid was eluted from the silica particles by incubation in 100 µl distilled water at 56° C. during 10 minutes. Finally, the silica particles were spun down again and the supernatant was carefully pipetted into fresh reaction tubes avoiding any carry-over of silica. Extracted nucleic acid samples were stored at −70° C. until use.

Prior to the detection of CMV mRNAs in these isolates, the integrity and amount of extracted RNA was validated. Therefore, samples were analyzed for the presence of U1 snRNP-specific A protein (U1A) mRNA (Sillekens, P.T.G., et al., EMBO J. 6, 3841–3848., 1987), being a relatively low abundant message, transcribed from a cellular housekeeping gene. As revealed by Northern blot analysis, presence of amplifiable U1A mRNA was obvious in all samples (data not shown).

1.1.3 Oligonucleotides used in amplification and as probes

Sequences and polarity of the oligonucleotides used in the amplification and the probes used for specific detection, are shown in Table 1.

All oligonucleotides were synthesized on a PCR-MATE 391 DNA synthesizer (Applied Biosystems) using phosphoramidite biochemistry. Oligonucleotides for ELGA detection (see below) were synthesized with a 5'-amino link (Aminolink 2; Applied Biosystems) for subsequent coupling of horseradish peroxidase (HRP).

Oligonucleotides used for amplification were purified by electrophoretically separating the crude oligonucleotide solutions over a 20% polyacrylamide/7M urea slab gel and subsequent elution of the full-length oligonucleotide from the corresponding gel band. After elution from the gel slices and concentration by ethanol precipitation, the oligonucleotides were dissolved in Milli-Q water and concentrations determined by OD(260 nm) measurement.

Oligonucleotides used as detection probes were conjugated with HRP (Boehringer) by coupling the enzyme to the amino link of the oligonucleotide using the cross-linking reagents SDPD (Pharmacia) and EMCS (Fluka). Unbound HRP was removed over a Qiagen Tip-100 column (Qiagen). The HRP-labeled oligonucleotides were purified by polyacrylamide gel electrophoresis and subsequent elution of the HRP-oligonucleotides from the gel slices by overnight incubation in water. The amount of HRP-conjugated oligonucleotide was calculated from OD(260 nm) and OD(400 nm) measurement. The solutions were stored at −70° C.
5'-CTGGAGATATATGTTGACCA-3'1.1.4 NASBA amplification RNA amplifications were performed using NASBA, since this amplification technology is capable of specifically amplifying RNA in a background of DNA. These amplification reactions were carried out using a standard NASBA protocol:

To set up an amplification reaction, 10 µl of 2.5 x reaction buffer [100 mM Tris-hydrochloric acid (pH 8.5); 30mM magnesium chloride; 105 mM Potassium chloride; 12.5 mM dithiothreitol; 2.5 mM of each of dNTP; 5 mM of ATP, CTP and UTP; 3.75 mM of GTP; 1.25 mM of ITP] was added to a reaction tube together with 6.25 µl 4 x mix [0.8 µM of each oligonucleotide used in the amplification; 60% dimethylsulphoxide], 5 µl nucleic acid solution, and 1.75 µl distilled water. This mixture was heated at 65° C. during 5 minutes, after which the tubes were placed at 41° C. Two µl of enzyme mix [40 units T7 RNA polymerase; 8 units AMV reverse transcriptase; 0.1 unit RNase H; 1.25 µg/µl BSA] were added and the contents of the tube were mixed by gentle tapping. The reaction was incubated at 41° C. for 90 minutes and stopped by placing it at −20° C.

1.1.5 Polymerase Chain Reaction

For the detection of the corresponding genes of the HCMV mRNAs PCR amplification was used (performed essentially as described in Saiki et al, 1985).

As template DNA, 5 µl nucleic acid solution were added to a total of 20 µl of reaction mixture for amplification containing the appropriate oligonucleotide pair (15 pmol each), deoxyribonucleoside triphosphates (200 µM each; Pharmacia), 2 µl of 10×PCR buffer (Perkin-Elmer), and 1.25 units Taq polymerase. Reactions were overlaid with 100 µl of mineral oil to prevent evaporation. The amplification was performed in a DNA thermal cycler (Perkin-Elmer) by 40 cycles of denaturation at 94' C. for 1 min, primer annealing at 60° C. for 1 min, chain extension at 72° C. for 2 min, and a final extension segment at 72° C. for 10 min.

1.1.6 Southern blot analysis of PCR-amplified products

Amplified DNA was transferred from a 2.0% Pronarose gel (Hispanagar, S. A.) to a nylon membrane (Zeta-probe; BioRad, USA) by vacuum blotting in 2×SSC [1×SSC is 150 mM sodium chloride; 15 mM sodium citrate] during 2 hours. Membranes were preincubated at 50° C. in a hybridization solution [0–5 M sodium phosphate (pH 7.2); 7% sodium dodecyl sulphate] during 30 minutes prior to the addition of 32P labeled oligonucleotide probe to a final concentration of about 105 cpm/ml. Hybridization was performed overnight at 50° C. Subsequent washings were carried out at 50° C. in 0.3×SSC supplemented with 0.1% SDS. Autoradiography was performed for several hours at −70° C. with Kodak Royal X-omat film and intensifying screens.

1.1.7 Analysis of NASBA-amplified products (ELGA)

For the analysis of NASBA products a non-radioactive enzyme linked gel assay (ELGA) based on liquid hybridization was used. Hybridization of amplification product to a specific HRP labeled oligonucleotide probe was performed by mixing 2 µl of an amplification reaction with 1 µl 5×SSC, 1 µl concentrated loading buffer [25% (v/v) glycerol; 10 mM sodium phosphate buffer (pH 7.0); 0.05% bromophenol blue; 0.01% xylene cyanol], and 1 µl HRP-labeled oligonucleotide solution containing about 1010 molecules per µl, followed by incubation at 45° C. during 15 minutes. After hybridization, half of the reaction mixture was directly applied onto a 7% polyacrylamide gel supplemented with 0.04% (w/v) dextran sulphate. After separation of bound and unbound HRP-labeled oligonucleotide by electrophoresis, the probe was visualized in the gel by direct staining with 50 ml substrate solution [125 µg 3,3',5,5'-tetramethylbenzidine per ml; 0.003% hydrogen peroxide; 100 mM sodium citrate buffer (pH 5.2)] for about 10 minutes at room temperature. Finally, the gel was fixed by overnight incubation in a 50% (v/v) methanol solution and air dried.

2.1 RESULTS:

2.1.1 Oligonucleotide pairs and sensitivity

To determine the analytical sensitivity attainable in NASBA with the oligonucleotide pairs a standard dilution series of in vitro generated CMV RNA was evaluated. An RNA template of known concentration was generated in vitro from a cloned subfragment of the CMV AD 169 EcoRI fragment J (Schrier, R. D., et al., Science 230, 1048–1051., 1985) for IEA and a CMV clone encompassing the pp67 gene for pp67. Standard dilution series were prepared from the in vitro generated RNA.

Sensitivity of the CMV-IEA (E4) oligonucleotide set was reproducibly found to be at least 100 molecules of in vitro generated RNA input in NASBA reaction. For the CMV-IEA(E2/E3) oligonucleotide pair a comparable sensitivity of 100 molecules could be achieved.

Oligonucleotide pair performance of the pp67 pairs was evaluated on in vitro generated RNA transcribed from a cloned fragment of the pp67 gene of CMV AD169. For the CMV-pp67-4 oligonucleotide pair, derived from AD169, NASBA conditions could be optimized such that the sensitivity of this pair was 100 molecules of in vitro generated RNA. As could be anticipated from the mismatches of the downstream primer of CMV-pp67-1, based on the Towne strain sequence, no amplification product could be generated with this oligonucleotide pair from the CMV AD169-derived pp67 RNA.

To establish whether in addition to in vitro generated RNA the genuine viral mRNAs could also be identified by these oligonucleotide sets, total nucleic acid from fibroblast cells infected with CMV AD 169 was extracted and amplified by NASBA. All oligonucleotide sets revealed hybridization signals on Northern blot that correspond to CMV specific RNA derived amplification products. Northern blot analysis was performed as described below.

exception of a single sample, all DNA-positive samples were positive for IEA-mRNA as well, pp67 mRNA could only be detected in a subset of the CMV-DNA positive patients (Table 2). In Table 3, the data for mRNA and DNA detection for the IEA target and the pp67 target are summarized. When the presence or absence of pp67 mRNA in these patients was correlated to their clinical status, a striking relation was observed between the presence of pp67 mRNA and possibly CMV-related clinical symptoms (Table 4). Two patients in this group showed symptoms of transplant rejection with graft dysfunction and fever. Clinical diagnoses in other patients were gastritis after heart transplantation and retinitis in a kidney transplant recipient. Retinitis was further observed in three CMV-pp67 mRNA positive AIDS patients, two of which also suffered from esophagitis.

TABLE 1

Primers and probes for PCR and NASBA amplification of CMV targets

| Primer pair | Oligo-nucleotides | Sequence | CMV target | SEQ ID NO. |
|---|---|---|---|---|
| CMV-IEA (E4) | CMV-IEA 1.1 | 5'-aattctaatacgactcactatagggagaCTTGCTCACATCATGCAGCT-3' | IEA-exon 4 | SEQ ID NO: 1 |
|  | CMV-IEA 1.2 | 5'-aattctaatacgactcactatagggagaCTTGGTCACATTATAGAGTT-3' |  | SEQ ID NO: 2 |
|  | CMV-IEA 2.1 | 5'-TGAGCCTTTCGAGGAGATGAA-3' |  | SEQ ID NO: 3 |
|  | CMV-IEA HRP-1 | 5'-AGGATAAGCGGGAGATGTGGAT-3' |  | SEQ ID NO: 4 |
| CMV-pp67-I | CMV-pp67 1.1 | 5'-aattctaatacgactcactatagggagaGGGTCGATTCGAGACCGA-3' | pp67 | SEQ ID NO: 5 |
|  | CMV-pp67 2.1 | 5'-GACCTGATATCCCTCCATATA-3' |  | SEQ ID NO: 7 |
|  | CMV-pp67 HPR-1 | 5'-GGATTCGGACTTTCCGTTCGA-3' |  | SEQ ID NO: 8 |
| CMV-pp67-4 | CMV-pp67 1.2 | 5'-aattctaatacgactcactatagggagaGGGTCGATTC-AGACTGA-3' | pp67 | SEQ ID NO: 9 |
|  | CMV-pp67 2.1 | 5'-GACCTGATATCCCTCCATATA-3' |  | SEQ ID NO: 7 |
|  | CMV-pp67 HRP-1 | 5'-GGATTCGGACTTTCCGTTCGA-3' |  | SEQ ID NO: 8 |

T7 promoter sequence in downstream primers is given in small characters.

Based on ten-fold dilution series of the recombinant plasmids used for in vitro transcription of IEA RNA or pp67 RNA, the lower detection limit of the NASBA oligonucleotide pairs, when used in PCR, was about 50–100 genome equivalents.

2.1.2 Detection of HCMV mRNA and DNA.

Because the internal U1A mRNA control was positive in all samples, the entire series of 35 specimens was further analyzed for the presence of the IEA gene and its corresponding mRNA. When amplification by PCR was performed, eighteen samples were positive for CMV-DNA when using the IEA gene primers (Table 2). However, PCR amplification with the pp67 gene primers failed to detect CMV-DNA in two of these eighteen samples (OT28 and OT34, Table 2). This indicates that despite the fact that already two oligonucleotide pairs were used for the pp67 gene, still two samples were falsely negative for CMV DNA. Most likely, this is due to sequence variation among the clinical strains in this part of the HCMV genome, since the sensitivity of the oligonucleotide sets for the IEA gene target and the pp67 gene target are comparable.

When the samples were analyzed for IEA mRNA by NASBA amplification with the same oligonucleotide pairs as used for DNA detection by PCR, essentially all samples that were positive by PCR were also found positive by NASBA. Therefore, with the exception of a single patient sample, in all specimens positive for CMV-IEA DNA the cognate mRNA could be detected as well.

Analysis for pp67 mRNA by NASBA revealed a strikingly different result. In contrast to IEA for which, with the

TABLE 2

Analysis of CMV-IEA and CMV-pp67 DNA and mRNA in clinical specimens

| No. | IEA-DNA (PCR) | IEA-mPNA (NASBA) | pp67-DNA (PCR) | pp67-mRNA (NASBA) |
|---|---|---|---|---|
| OT01 | − | − | − | − |
| OT02 | ++ | ++ | ++ | ++ |
| OT03 | − | − | − | − |
| OT04 | ++ | (+) | ++ | ++ |
| OT06 | − | − | − | − |
| OT07 | + | + | (+) | − |
| OT09 | + | ++ | (+) | − |
| OT10 | − | − | − | − |
| OT11 | − | − | − | − |
| OT12 | ++ | ++ | ++ | (+) |
| OT13 | ++ | ++ | ++ | (+) |
| OT14 | ++ | ++ | ++ | ++ |
| OT16 | − | − | − | − |
| OT17 | ++ | ++ | ++ | (+) |
| OT18 | − | − | − | − |
| OT19 | ++ | ++ | (+) | − |
| OT20 | − | − | − | − |
| OT21 | − | − | − | − |
| OT22 | ++ | ++ | ++ | ++ |
| OT23 | − | − | − | − |
| OT24 | ++ | ++ | ++ | ++ |
| OT26 | ++ | ++ | + | − |
| OT27 | − | − | − | − |
| OT28 | (+) | ++ | − | − |
| OT29 | ++ | ++ | ++ | − |

TABLE 2-continued

Analysis of CMV-IEA and CMV-pp67 DNA and mRNA in clinical specimens

| No. | IEA-DNA (PCR) | IEA-mPNA (NASBA) | pp67-DNA (PCR) | pp67-mRNA (NASBA) |
|---|---|---|---|---|
| 0T31 | ++ | ++ | ++ | ++ |
| 0T32 | – | – | – | – |
| 0T33 | ++ | + | ++ | ++ |
| 0T34 | (+) | – | – | – |
| 0T35 | – | – | – | – |
| 0T36 | – | – | – | – |
| 0T37 | – | – | – | – |
| 0T38 | – | – | – | – |
| 0T39 | – | – | – | – |
| 0T40 | (+) | ++ | (+) | – |

No. patient sample number
+ positive
++ strongly positive
(+) weakly positive

| CMV target | DNA-pos/ RNA-pos | DNA-pos/ RNA-neg | DNA-neg/ RNA-neg |
|---|---|---|---|
| IEA (n = 35) | 17 | 1 | 17 |
| pp67 (n = 35) | 9 | 7 | 19 |

*Two samples negative for pp67 DNA and RNA while positive for IEA DNA and RNA.

*A number of CMV-positive samples do not contain detectable levels of pp67 mRNA.

TABLE 4

Correlation between presence of HCMV pp67 mRNA and clinical status.
A. pp67 DNA-pos/RNA-pos patients

| Patient | Clinical status |
|---|---|
| Heart transplantation | graft rejection, fever, bronchial carcinoma, |
| Kidney transplantation | immunocytoma |
| Kidney transplantation | retinitis, fever |
| Kidney transplantation | graf rejection, fever |
| AIDS | |
| AIDS | retinitis, lobular hepatitis |
| AIDS | retinitis, esophagitis |
| Heart transplantation | retinits, esophagitis |
| AIDS | gastritis |
| | epilepsy |

B. pp67 DNA-pos/RNA-neg patients

| Patient | Clinical status |
|---|---|
| AIDS | Kaposi sarcoma, cryptococcus meningitis |
| AIDS | |
| Kidney transplantation | |
| Kidney transplantation | |
| Heart transplantation | |
| Heart transplantation | secundary EBV infection, immunocytoma |
| Heart transplantatin | |

C. pp67 DNA-neg/RNA-neg patients

| Patient | Clinical status |
|---|---|
| Leukemia | |
| Liver transplantation | elevated liver enzymes |
| Heart transplantation | graft rejection |
| Heart transplantation | graft rejection |
| Heart transplantation | |
| AIDS | lobular pneumonia, candida infection |
| — | acute myeloid leukemia, vasculitis |
| Heart transplantation | |
| — | primary EBV mononucleosis |
| Kidney transplantation | |
| AIDS | |
| Heart transplantatoin | graft rejection |
| AIDS | |
| Kidney transplantation | tuberculosis |
| — | myelodysplastic syndrome |
| Heart transplantation | seisure |
| Heart transplantation | sternum infection, staphylococcus aureas |
| Heart transplantation | |
| Heart transplantation | |

Example 2
Analytical sensitivity of CMV-pp67 oligonucleotides in amplification and detection.

2.1. Materials and methods 2.1.1. In vitro RNA

RNA with a length of 1125 nucleotides encompassing 338 nucleotides of the CMV mRNA encoding the pp67 matrix tegument protein was synthesized in vitro from a cloned fragment of the corresponding gene by T7 RNA polymerase-based transcription. Prior to transcription, plasmid DNA was linearized by Bam HI digestion, the unique restriction site of which is located about 800 base pairs (bp) downstream of the CMV insert. The digested DNA was purified by phenol extraction and concentrated by ethanol precipitation. Transcription from the linearized plasmid DNA was performed in transcription buffer [40 mM Tris-Hydrochloric acid (pH 7.5); 6 mM Magnesium chloride; 2 mM Spermidine; 10 mM Sodium chloride] supplemented with 0.5 mM of each rNTP, 10 mM Dithiothreitol (DTT), 1 unit per $\mu l$ RNA Guard (Pharmacia), and about 500 units T7 RNA Polymerase (Pharmacia). After 4 hours incubation at 37° C., DNase I (Boehringer) was added to a final concentration of 0.1 unit per $\mu l$ and the reaction mixture incubated at 37° C. for an additional 30 minutes. Subsequently, in vitro generated RNA was purified from the reaction mixture using a RNeasy RNA Purification kit (Qiagen). Finally, the concentration of the in vitro RNAs was determined by OD (260 nm) measurement and appropriate serial dilutions in water were stored at −70° C.

2.1.2. Oligonucleotides used in amplification and as probes

Sequences and polarity of the oligonucleotides used in the amplification and of the probes used for specific detection, are shown in Table 5.

All oligonucleotides were synthesized on a PCR-MATE 391 DNA synthesizer (Applied Biosystems) using phosphoramidite biochemistry. Oligonucleotides for ELGA detection (see below) were synthesized with a 5'-amino link (Aminolink 2; Applied Biosystems) for subsequent coupling of horseradish peroxidase (HRP).

Oligonucleotides used in amplification were purified by electrophoretically separating the crude oligonucleotide solutions over a 20% polyacrylamide/7M Urea slab gel and subsequent elution of the full-length oligonucleotide from the corresponding gel band. After elution from the gel slices and concentration by ethanol precipitation, oligonucleotides were dissolved in Milli-Q water and concentrations determined by OD(260 nm) measurement.

For ELGA detection, oligonucleotide probe CMV-pp67 HRP1 was conjugated with HRP (Boehringer) by coupling the enzyme to the amino link of the oligonucleotide using the cross-linking reagents SDPD (Pharmacia) and EMCS (Fluka). Unbound HRP was removed over a Qiagen Tip-100 column (Qiagen). The HRP-labeled oligonucleotide was purified by polyacrylamide gel electrophoresis and subsequent elution of the HRP-oligonucleotide from the gel slices by overnight incubation in water. The amount of HRP-conjugated oligonucleotide was calculated from OD(260 nm) and OD(400 nm) measurement. The solutions were stored at −70° C.

For ECL detection, oligonucleotide probe CMV-pp67-ECL (Table 5) was conjugated with the ECL label by incubating the amino link oligonucleotide with TAG NHS-Ester (Igen). Unbound label was removed by passing the reaction mixture over a Qiagen Tip-100 column (Qiagen). The amount of ECL-labelled oligonucleotide was calculated from OD (260 nm) and OD (460 nm) measurement. The solution was stored at −70° C. and used without further purification.

2.1.3. NASBA amplification

RNA amplifications were performed using the NASBA amplification technology. To set up a NASBA amplification reaction, a premix was generated by mixing 4 μl of 5×reaction buffer [200 mM Tris-hydrochloric acid (pH 8.5), 350 mM potassium chloride, 60 mM magnesium chloride, 25 mM DTT, 5 mM of each dNTP, 10 mM of ATP, CTP and UTP, 7.5 mM of GTP and 2.5 mM of ITP] with 2 μl sugar solution [15% (w/v) sucrose, 5% (w/v) mannitol, 5% (w/v) dextran T40] and 4 μl of a mix containing 1 μM of each oligonucleotide to be used in the amplification in 75% DMSO. Of this premix, 10 μl was added to 5 μl nucleic acid solution and incubated during 5 minutes at 65° C. Subsequently, the reaction tubes were incubated at 41° C. during 5 minutes before 5 μl enzyme mix [32 units T7 RNA polymerase; 6.4 units AMV reverse transcriptase; 0.08 unit RNase H; 2.1 μg BSA; 20 mM DTT; 1.5 M sorbitol] was added. After the final addition, tubes were mixed by gentle tapping, centrifuged, and incubated at 41° C. during 90 minutes. Reactions were stopped by placing them at −20° C.

2.1.4. Analysis of NASBA-amplified reaction products by ELGA

For the analysis of NASBA reaction products a non-radioactive enzyme linked gel assay (ELGA) based on liquid hybridization was used. Hybridization of amplification product to a specific HRP-labelled oligonucleotide probe was performed by mixing 3 μl of a NASBA amplification reaction with 1 μl 6×SSC, 1 μl concentrated loading buffer [25% (v/v) glycerol; 10 mM sodium phosphate buffer (pH 7.0); 0.05% bromophenol blue; 0.01% xylene cyanol], and 1 μl HRP-labelled oligonucleotide CMV-pp67 HRP1 (Table 5) stock solution, followed by incubation at 45° C. during 15 minutes. After hybridization, half of the reaction mixture was directly applied onto a 7% polyacrylamide gel supplemented with 0.04% (w/v) dextran sulphate. After separation of bound and unbound HRP-labeled oligonucleotide by electrophoresis, the probe was visualized in the gel by direct staining with 50 ml substrate solution [125 μg 3,3',5,5'-tetramethylbenzidine per ml; 0.003% hydrogen peroxide; 100 mM sodium citrate buffer (pH 5.2)] for about 10 minutes at room temperature. Finally, the gel was fixed by overnight incubation in a 50% (v/v) methanol solution and air dried.

2.2. Results 2.2.1. Analytical sensitivity of CMV-pp67 oligonucleotides when used in NASBA To determine the analytical sensitivity of the improved CMV-pp67 NASBA pair of oligonucleotides according to the present invention (CMV-pp67-5) and to compare this sensitivity with the analytical sensitivity of the CMV-pp67-4 NASBA pair (Table 5), a dilution series of in vitro generated RNA encompassing the target sequence of both pairs was prepared. The individual samples of this dilution series contained 10,000, 1,000, 100 and 10 molecules of in vitro generated RNA, respectively. In several independent experiments NASBA amplification of this dilution series was performed with these two CMV-pp67 NASBA pairs of oligonucleotides (Table 5). A typical example is shown in Table 6.

Direct comparison of the pairs showed that in this Example the lowest amount of in vitro RNA molecules that could be detected with CMV-pp67-4 was 1,000 molecules, whereas with the improved combination CMV-pp67-5 also 100 molecules of input RNA revealed a positive NASBA result.

Table 7 summarizes the results of five independent experiments. For each pair, the lowest in vitro RNA amount still giving a positive NASBA result in a particular experiment is shown.

The pairs that were analyzed have a comparable analytical sensitivity in NASBA, since with both combinations presence of 100 molecules of in vitro generated RNA in a sample can be demonstrated upon NASBA amplification. However, in three out of five analyses the CMV-pp67-4 combination appeared to have a lower detection limit of 1,000 molecules of in vitro generated RNA, whereas CMV-pp67-5 consistently revealed a positive NASBA result for 100 molecules of input RNA in all analyses that were performed (Table 7).

Therefore, the CMV-pp67-5 combination was regarded as more robust for NASBA amplification. It was anticipated that this advantageous aspect of this novel pair of oligonucleotides does not only hold true for the detection of in vitro generated RNA, but also for detection of the genuine CMV-pp67 protein encoding mRNA as encountered in clinical specimens of CMV infected individuals.

Example 3

Detection of CMV-pp67 protein encoding mRNA in clinical samples.

3.1. Materials and methods 3.1.1. Clinical specimens 495 samples were obtained from a cohort of 134 AIDS patients. These ethylenediamine tetraacetic acid (EDTA) anticoagulated whole blood samples submitted consecutively as received by the laboratory, were mixed with nine volumes of lysis buffer [50 mM Tris-hydrochloric acid (pH 6.4); 20 mM EDTA; 1.3% (w/v) Triton X-100; 5.25 M guanidinium thiocyanate] and stored at −70° C. until use.

3.1.2. Oligonucleotides

Sequences and polarity of the oligonucleotides used in amplification and of the probes used for specific detection, are shown in Table 5. For further details is referred to paragraph 2.1.2. in the Materials and Methods section of Example 2.

3.1.3. Nucleic acid isolation

From the anticoagulant-treated blood specimens total nucleic acid was isolated using guanidinium thiocyanate-mediated cell lysis and adsorption of nucleic acid to silica particles (Boom et al., J. of Clin. Microbiol. 28, 495–503, 1990).

Whole blood samples in Lysis buffer were thawed and from each sample 1 ml (equivalent to 100 μl whole blood) was transferred into an Eppendorf tube. Subsequently, 50 μl of hydrochloric acid-activated silicum dioxide particles [size-selected suspension of 1 mg/ml in 0.1 M hydrochloric acid (Sigma); see ref. Boom et al., 1990] were added and the suspension was incubated during 10 minutes at room temperature with regular vortexing. Nucleic acid bound to the silica was spun down by centrifugation. Pelleted silica particles were washed twice with 1 ml GuSCN wash buffer [50 mM Tris-hydrochloric acid (pH 6.4); 5.25 M guanidinium thiocyanate], followed by two washing steps with 1 ml 70% ethanol and a single washing step with 1 ml acetone. After each washing step, the suspension was briefly centrifuged and the silica pellet was resuspended in the next washing solution by thorough mixing. After removal of the acetone, the silica particles were dried by incubation at 56° C. in a heating block during 10 minutes. Nucleic acid was eluted from the silica particles by incubation in 50 μl Tris-buffered elution medium (pH 7.5) at 56° C. during 10 minutes. Finally, the silica particles were spun down again and the supernatant was carefully pipetted into fresh reaction tubes avoiding any carry-over of silica. Extracted nucleic acid samples were stored at −70° C. until use.

3.1.4. NASBA amplification

For amplification, a so-called accusphere containing all the ingredients necessary for a NASBA reaction (see "NASBA amplification" paragraph in the Materials and Methods section of Example 2) in a lyophilized form, was reconstituted in a Tris-HCl (pH 8.5) buffered solution of 30% (v/v) DMSO. Subsequently, for is each sample to be analysed, 5 μl nucleic acid solution and 10 μl of the oligonucleotide solution were added to a test tube. The resulting mixtures were heated at 65° C. for 5 minutes, after which the tubes were placed at 41° C. After 5 minutes incubation at 41° C., 5 μl of enzyme solution containing 32 units T7 RNA polymerase, 6.4 units of AMV reverse transcriptase and 0.08 unit RNase H were added and the contents of the tube were mixed by gentle tapping. The reactions were incubated at 41° C. for 90 minutes in a water bath. Reactions were stopped by placing them at −20° C.

3.1.5. Analysis of NASBA amplified reaction products by ECL detection

For electrochemiluminescence (ECL) based analysis, detection reagents were prepared by vortexing a capture probe solution, containing biotinylated capture probe CMV-pp67 CAP (Table 5) immobilized on streptavidin-coated paramagnetic beads (Dynal), until an opaque solution was formed and subsequently mixing 10 μl of this suspension (containing 3.4×105 beads loaded with capture probe) and 10 μl of a CMV-pp67-ECL (Table 5) probe solution (containing 3.4×1011 molecules of ECL labeled probe) into fresh reaction tubes. To these mixtures, 5 μl of a two-fold diluted NASBA reaction was added and incubated during 30 minutes at 41° C. During hybridization, the tubes were mixed every 10 minutes. Subsequently, 300 μl NASBA QR System Assay buffer (Organon Teknika) were added to each hybridization tube and the tubes were positioned in a NASBA QR System for automated reading of ECL signals.

3.2. Results 3.2.1. Detection of CMV-pp67 mRNA in clinical samples with two different pairs of oligonucleotides.

Whole blood samples from patients clinically at risk of infection with CMV were analysed for the presence of CMV mRNA encoding the matrix tegument protein pp67 (CMV-pp67 mRNA) with the two distinct pairs of oligonucleotides (Table 5) suited for NASBA amplification.

In total, 495 samples from AIDS patients, previously analysed by NASBA amplification with combination CMV-pp67-4 (Table 5), now were reanalyzed under similar NASBA conditions with the improved pair CMV-pp67-5 which is the object of the present invention. In Table 8, the results obtained with either of the pairs are shown and compared to each other.

Although from earlier experiments no (statistically) significant difference in the analytical sensitivity of these sets of oligonucleotides could be determined (due to the fact that only a few samples were tested; see Example 2), the improved CMV-pp67-5 set appeared to be much better for the detection of CMV-pp67 mRNA by NASBA in nucleic acid solutions extracted from whole blood samples. Due to the amount of samples (n=495), this difference is also statistical significant.

In 65 samples, the improved pair CMV-pp67-5 revealed a positive NASBA result, whereas NASBA reactions performed with the CMV-pp67-4 pair were negative. In only 9 cases (of which 5 samples are difficult to interpret) it was the other way around.

In conclusion, apart from being more robust than the CMV-pp67-4 set (see Example 2), the novel and improved pair of oligonucleotides according to the present invention (CMV-pp67-5) also appears to be superior in the detection of CMV-pp67 mRNA in clinical samples.

TABLE 5

Oligonucleotides used in NASBA amplification and detection of CMV-pp67 mRNA

| Pair | Oligonucleotides | SEQ ID NO: | Sequence |
|---|---|---|---|
| CMV-pp67-4 | CMV-pp67 P1.2 | SEQ ID NO: 9 | 5'-aattctaatacgactcactatagggagaGGGTCGATTCAGACTGA-3' |
| | CMV-pp67 P2.1 | SEQ ID NO: 7 | 5'-GACCTGATATCCCTCCATATA-3' |
| | CMV-pp67 HRP1 | SEQ ID NO: 8 | 5'-GGATTCGGACTTTCCGTTCGA-3' |
| CMV-pp67-5 | CMV-pp67 P1.2 | SEQ ID NO: 9 | 5'-aattctaatacgactcactatagggagaGGGTCGATTCAGACTGA-3' |
| | CMV-pp67 P2.4 | SEQ ID NO: 11 | 5'-CTGGAGATATATGTTGACCA-3' |
| | CNV-pp67-CAP | SEQ ID NO: 8 | 5'-BIO-GGATTCGGACTTTCCGTTCGA-3' |
| | CNV-pp67-ECL | SEQ ID NO: 12 | 5'-ECL-CCAAAAAGCTAGCCGTCACG-3' |

The T7 promoter is given small letters.

TABLE 6

Analytical sensitivity of two CMV-pp67 pairs of oligonucleotides when used in NASBA.

| | ELGA result | |
|---|---|---|
| Input RNA | CMV-pp67-4 | CMV-pp67-5 |
| $10^4$ | + | + |
| $10^3$ | + | + |
| $10^2$ | − | + |
| $10^1$ | − | − |

TABLE 7

Comparison of two CMV-pp67 pairs of olgionucleotides used in NASBA.

| | Lower detection limit* | |
|---|---|---|
| Experiment | CMV-pp67-4 | CMV-pp67-5 |
| 1 | $10^3$ | $10^2$ |
| 2 | $10^2$ | $10^2$ |
| 3 | $10^2$ | $10^2$ |
| 4 | $10^2$ | $10^2$ |
| 5 | $10^3$ | $10^2$ |

*Lower detection limit: lowest amount of input RNA that still reveals a positive NASBA result

TABLE 8

Analysis of CMV-pp67 mRNA oligonucleotides in amplifications performed on clinical specimens (n = 495)

| | | novel CMV-pp67-5 oligo's | |
|---|---|---|---|
| | | positive | negative |
| (known) | positive | 53(10)* | 4(5)* |
| CMV-pp67-4 oligo's | negative | 65 | 358 |

*between brackets the number of weakly positive samples obtained with the CMV-pp67-4 pair is given

---

We claim:

1. An oligonucleotide corresponding to part of a nucleic acid sequence encoding HCMV pp67, said oligonucleotide being 10–35 nucleotides in length and comprising at least a fragment of 10 nucleotides of a sequence selected from the group consisting of:

5'-GGGTCGATTCAGACTGA-3' [SEQ.ID.No.: 10],
5'-CTGGAGATATATGTTGACCA-3' [SEQ.ID.No.: 11],
5'-GGATTCGGACTTTCCGTTCGA-3' [SEQ.ID.No.: 8], and
5'-CCAAAAAGCTAGCCGTCACG-3' [SEQ.ID.No.: 12], or its complementary sequence.

2. A method for the diagnosis of cytomegalovirus (CMV) disease in an individual suspected of having CMV disease, comprising:

(1) isolating a nucleic acid from a blood sample from said individual, which nucleic acid may contain mRNA that encodes a late structural protein PP67 of human CMV, and adding thereto a primer pair and amplification reagents which will amplify a target sequence within said mRNA, and allowing the amplification of said target sequence to proceed;

(2) reacting the sample from step (1) with a labeled nucleic acid probe having a sequence complementary to part of the target sequence, and (3) detecting hybrids formed between the target sequence and the probe, wherein the detection of said hybrids indicates a positive diagnosis for CMV disease.

3. The method according to claim 2, wherein the mRNA is amplified using a transcription based amplification technique.

4. The method according to claim 3, wherein said amplification technique is nucleic acid sequence-based amplification (NASBA).

* * * * *

UNITED STATES PATENT AND TRADEMARK OFFICE
CERTIFICATE OF CORRECTION

PATENT NO.    : 6,306,602 B1
DATED         : October 23, 2001
INVENTOR(S)   : Sillekens et al.

Page 1 of 1

It is certified that error appears in the above-identified patent and that said Letters Patent is hereby corrected as shown below:

<u>Title page,</u>
Item [63], Related U.S. Application Data, after "now abandoned" please add -- which claims the benefit under 35 USC § 371 from PCT Application No. PCT/EP95/03295, filed Aug. 18, 1995, which claims the benefit of European Application 94202360.7, filed Aug. 18, 1994 --

Signed and Sealed this

Twentieth Day of August, 2002

Attest:

JAMES E. ROGAN
Attesting Officer   Director of the United States Patent and Trademark Office

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 48 base pairs
      (B) TYPE: nucleic acid
      (C) STRANDEDNESS: single
      (D) TOPOLOGY: unknown (ii) MOLECULE TYPE: cDNA to mRNA (xi) SEQUENCE DESCRIPTION: SEQ ID NO: 1:

AATTCTAATA CGACTCACTA TAGGGAGACT TGCTCACATC ATGCAGCT       48

(2) INFORMATION FOR SEQ ID NO: 2:

(i) SEQUENCE CHARACTERISTICS:
      (A) LENGTH: 48 base pairs
      (B) TYPE: nucleic acid
      (C) STRANDEDNESS: single
      (D) TOPOLOGY: unknown (ii) MOLECULE TYPE: cDNA to mRNA (xi) SEQUENCE DESCRIPTION: SEQ ID NO: 2:

AATTCTAATA CGACTCACTA TAGGGAGACT TGGTCACATT ATAGAGTT       48

(2) INFORMATION FOR SEQ ID NO: 3:

(i) SEQUENCE CHARACTERISTICS:
      (A) LENGTH: 21 base pairs
      (B) TYPE: nucleic acid
      (C) STRANDEDNESS: single
      (D) TOPOLOGY: unknown (ii) MOLECULE TYPE: cDNA to mRNA (xi) SEQUENCE DESCRIPTION: SEQ ID NO: 3:

TGAGCCTTTC GAGGAGATGA A       21

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: cDNA to mRNA (xi) SEQUENCE DESCRIPTION: SEQ ID NO: 4:

AGGATAAGCG GGAGATGTGG AT                        22

(2) INFORMATION FOR SEQ ID NO: 5:

(i) SEQUENCE CHARACTERISTICS:
        (A) LENGTH: 46 base pairs
        (B) TYPE: nucleic acid
        (C) STRANDEDNESS: single
        (D) TOPOLOGY: unknown (ii) MOLECULE TYPE: cDNA to mRNA (xi) SEQUENCE DESCRIPTION: SEQ ID NO: 5:

AATTCTAATA CGACTCACTA TAGGGAGAGG GTCGATTCGA GACCGA      46

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (ii) MOLECULE TYPE: cDNA to mRNA (xi) SEQUENCE DESCRIPTION: SEQ ID NO: 6:

GGGTCGATTC GAGACCGA                              18

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: cDNA to mRNA (xi) SEQUENCE DESCRIPTION: SEQ ID NO: 7:

GACCTGATAT CCCTCCATAT A                        21

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: cDNA to mRNA (xi) SEQUENCE DESCRIPTION: SEQ ID NO: 8:

GGATTCGGAC TTTCCGTTCG A                        21

(2) INFORMATION FOR SEQ ID NO: 9:

```
    (i) SEQUENCE CHARACTERISTICS:
        (A) LENGTH: 45 base pairs
        (B) TYPE: nucleic acid
        (C) STRANDEDNESS: single
        (D) TOPOLOGY: unknown (ii) MOLECULE TYPE: cDNA to mRNA (xi) SEQUENCE DESCRIPTION: SEQ ID NO: 9:

AATTCTAATA CGACTCACTA TAGGGAGAGG GTCGATTCAG ACTGA              45

(2) INFORMATION FOR SEQ ID NO: 10:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: cDNA to mRNA (xi) SEQUENCE DESCRIPTION: SEQ ID NO: 10:

GGGTCGATTC AGACTGA                                             17

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: cDNA to mRNA (vi) ORIGINAL SOURCE:
        (A) ORGANISM: Cytomegalovirus (xi) SEQUENCE DESCRIPTION: SEQ ID NO: 11:

CTGGAGATAT ATGTTGACCA                                          20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: cDNA to mRNA (vi) ORIGINAL SOURCE:
        (A) ORGANISM: Cytomegalovirus (xi) SEQUENCE DESCRIPTION: SEQ ID NO: 12:

CCAAAAAGCT AGCCGTCACG                                          20
```